United States Patent [19]

Intille

[11] 4,008,266
[45] Feb. 15, 1977

[54] COUPLING OF AROMATIC COMPOUNDS IN THE PRESENCE OF MOLECULAR OXYGEN, A MERCURIC OXYANION COMPOUND, AND A GROUP VIII METAL OR GROUP VIII METAL OXYANION COMPOUND

[75] Inventor: George M. Intille, Maryland Heights, Mo.

[73] Assignee: Monsanto Company, St. Louis, Mo.

[22] Filed: Jan. 2, 1974

[21] Appl. No.: 430,280

Related U.S. Application Data

[63] Continuation-in-part of Ser. No. 302,713, Oct. 18, 1973, abandoned.

[52] U.S. Cl. .................... 260/475 R; 260/346.2 R; 260/346.2 M; 260/457; 260/479 R; 260/488 CD; 260/515 P; 260/556 AR; 260/578; 260/592; 260/609 R; 260/612 R; 260/613 R; 260/618 R; 260/620; 260/645; 260/649 DP; 260/670

[51] Int. Cl.² ........................................ C07C 69/76
[58] Field of Search ................ 260/515 P, 346.2 M, 260/612 R, 620, 670, 613 R, 475 R, 479 R, 592, 645, 649 DP

[56] References Cited

UNITED STATES PATENTS 3,539,622  11/1970  Heck .................................. 260/515
3,728,409  4/1973  Selwitz .......................... 260/668 C

OTHER PUBLICATIONS

Unger et al., Journal of Organic Chemistry, (1969, Jan.), vol. 34, No. 1, pp. 18–21.
Itatani et al., Chemistry and Industry, June 12, 1971, pp. 674–675.
Itatani et al., J. of Org. Chem., vol. 38, No. 1, Jan. 1973, pp. 76–79.
Yoshimoto et al., J. of Catalysis, vol. 31, Oct. 1973, pp. 8–12.

*Primary Examiner*—Henry R. Jiles
*Assistant Examiner*—Bernard I. Dentz
*Attorney, Agent, or Firm*—Henry Croskell; Thomas B. Leslie

[57] ABSTRACT

A catalytic process in which molecular oxygen is used to couple aromatic compounds to form a variety of polyaromatic compounds is disclosed. The process comprises reacting monoaromatic compounds in the presence of molecular oxygen and a catalyst system comprising a mercuric oxyanion compound, a Group VIII metal, or metal oxyanion compound and optionally a redox reagent consisting of a soluble salt of a multivalent metal having an oxidation potential greater than that of the Group VIII metal.

30 Claims, No Drawings

COUPLING OF AROMATIC COMPOUNDS IN THE PRESENCE OF MOLECULAR OXYGEN, A MERCURIC OXYANION COMPOUND, AND A GROUP VIII METAL OR GROUP VIII METAL OXYANION COMPOUND

RELATED APPLICATION

This application is a continuation-in-part of copending application Ser. No. 302,713, filed Oct. 18, 1973 and now abandoned.

BACKGROUND OF THE INVENTION

This invention relates to the use of molecular oxygen for the coupling of aromatic compounds including substituted aromatics such as phenols or alkyl benzenes to form polyaromatic compounds such as phenylphenol, dimethylbiphenyl, dicarboxylic acid biphenyl and others.

Coupled aromatic compounds and particularly substituted coupled aromatic compounds have been found to be useful, environmentally safe functional fluids. Disubstituted polyaromatic compounds are also suitable as polymer intermediates. Polymers formed from such monomers will have aromatic backbones and have properties normally associated with such polymers such as high temperature resistance and flame retardancy.

It has been customary to couple benzene to form diphenyl by passing benzene through a hot tube heated to 650° to 850° C. Such a reaction is not suitable for producing substituted diphenyls from substituted benzenes. Such severe conditions usually attack the substituent causing an unwanted loss of reactant and reaction product. When substituted biphenyls are desired, one method frequently employed is the halogenation of the substituted benzene followed by the reaction of that compound at an elevated temperature around 300° C in the presence of copper powder. The reaction produces a low yield, however, and is additionally expensive due to the large amount of copper powder converted to the halide. The above reaction is furthermore not generally applicable to substituted aromatics since the severity of the reaction conditions precludes the use of many substituted aromatic compounds.

It has been known that certain metal compounds can act as oxidizing agents and can be used to couple aromatics under somewhat milder conditions. These certain metals in high oxidation states can be used to form diaromatics while they are simultaneously reduced to a lower valence state. Diphenyl mercury has been shown to form biphenyl and metallic mercury and palladium acetate has been shown to form diaromatics and metallic palladium. Because expensive metallic salts are used stoichiometrically in these reactions they are of little practical value. Until now it has not been possible to use inexpensive oxidizing agents such as molecular oxygen to effect this coupling.

It has more recently been known that coupling of aromatics may be made catalytic with respect to palladium through the use of acyl mercury complexes; however, the ac 1 mercury salt is used in stoichiometric quantities. The coupling reaction requires a stoichiometric amount of mercuric salt to be reduced for each molecule of coupled product formed. An additional palladium catalytic coupling reaction couples the aromatics in the presence of a strong acid which reduces the utility of the reaction. Aromatics with substituents sensitive to acid, for example, toluene produces a major product as a result of side chain oxidation.

Attempts to use standard methods to reoxidize the expensive oxidizing agents previously known in the art have resulted only in methods which are prohibitively expensive or in which conditions were so severe that poor yields resulted.

I have now found that these problems can be circumvented through the use of a catalyst comprised of a Group VIII metal or metal oxyanion compound and a mercuric oxyanion compound in the presence of molecular oxygen at pressures of at least about 200 psi. Only catalytic amounts of the Group VIII metal or metal oxyanion compound and the mercuric oxyanion compound are utilized with the molecular oxygen to provide a process for coupling monoaromatic compounds.

SUMMARY OF THE INVENTION

Providing a process for converting unsubstituted as well as substituted benzenes, especially alkylbenzenes and hydroxybenzenes, to the corresponding diphenyls, phenyl ethers and the like in good yield under relatively mild reaction conditions and using inexpensive molecular oxygen as the oxidizing agent without the requirements of a strong acid or stoichiometric amounts of the Group VIII metal or mercuric compound, represents an important advance in the art. The foregoing represents a principal object of this invention.

The present invention comprises a catalytic process for coupling aromatic compounds of the formula

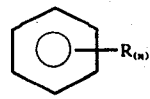

where
n is an integer from 0 to 5 and each of the R groups is hydroxy, alkoxy, alkyl, acyl, alkanoate, aryloxy, aryl, alkaryl, aralkyl, hydroxylated monovalent hydrocarbon, halogen, nitro, cyano, amino, carboxyl, carboxylic ester or sulfate and where any two R groups, located on adjacent carbon atoms of the benzene ring, can be joined to form a carbocyclic or heterocyclic ring, with molecular oxygen to produce coupled aromatic compounds comprising coupling said aromatic compounds with molecular oxygen in the presence of a mercuric oxyanion compound and a Group VIII metal oxyanion compound. The invention is also comprised of a catalytic process for coupling aromatic compounds of the formula

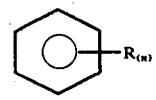

where
n is an integer from 0 to 5 and each of the R groups is hydroxy, alkoxy, alkyl, aryloxy, aryl, acyl, alkanoate, halogen or nitro, and where any two R groups, located on adjacent carbon atoms of the benzene ring, can be joined to form a carbocyclicor heterocyclic ring with molecular oxygen to produce coupled aromatic compounds comprising coupling said aromatic compounds with at least about 200 psi molecular oxygen in the presence of a mercuric oxyanion compound and a Group VIII metal or metal oxyanion compound. The above process is of particular value in preparing compounds such as phenylphenol, diphenyl, diphenyl ether, dimethyldiphenyl, dicarboxylic acid diphenyl, dimethoxydiphenyl, bis-phenoxy diphenyl, dibenzofuran and other and compounds which are of commercial value as heat exchange fluids, functional fluids, fiber intermediates, and plasticizer intermediates.

DESCRIPTION OF THE PREFERRED EMBODIMENTS

Compounds of the above formula, useful as reactants in the process of this invention, include a wide variety of aromatic compounds. If the integer $n$ is zero, the compound will be benzene. As $n$ increases in value, a larger and larger number of substituted benzenes are included within the scope of the formula. The integer $n$ has a maximum value of 5, however, since at least one carbon atom in the benzene ring must be unsubstituted for the catalyzed coupling reaction of this invention to take place. Preferred values for the integer $n$ are 0 to 2.

The R groups in the formula can be any groups which do not interfere with the aromatic ring coupling under the conditions of the reaction. Examples of suitable R groups include hydroxy, alkoxy, aryloxy, alkyl, aryl, alkaryl, aralkyl, acyl, alkanoate, hydroxylated monovalent hydrocarbon, halogen, nitro, cyano, amino, carboxyl, carboxylic ester or sulfate groups. The hydrocarbon substituent can be of any size having from 1 to 20 or more carbon atoms.

From a practical standpoint, each hydrocarbon substituent will seldom have more than 12 carbon atoms and usually not more than 6 carbon atoms. Hydroxy groups, either singly or in combination with other hydroxy groups or other dissimilar groups, are preferred. Also preferred are alkoxy groups. Alkyl groups and carboxylic acid and esters are particularly preferred groups. Examples of suitable R groups are methoxy, ethoxy, decyloxy, phenoxy, tolyloxy, xylyloxy, methyl, ethyl, cyclohexyl, dodecyl, phenyl, diphenyl, tolyl, xylyl, benzyl, phenylethyl, 2-ethylphenyl, formyl, acetyl, acetate, propionate, fluoro, chloro, bromo and iodo, nitro, carboxyl, alkyl carboxylate, acetate and propionate groups.

When one or more of the R groups are phenyl or phenoxy, the reactant suitable for use in this invention may be the same as, or closely similar to, some of the products obtained by means of the reaction. Put another way, some of the reaction products can be further reacted to form other polyaromatic compounds having more than two aromatic rings. Diphenyl, terphenyl, diphenyl ether and phenylphenol are examples of such reactants.

The substituents on any two adjacent carbon atoms in the aromatic ring can also be joined to form a carbocyclic or heterocyclic ring, thereby forming a condensed ring structure. Typical condensed ring compounds include naphthalene, benzofuran, indene and chlorobenzofuran. Other examples of suitable reactants are benzene, toluene, xylene, ethylbenzene, substituted naphthalenes, phenol, anisole, ethoxybenzene, phenyl acetate, phenyl hexanoate, phenoxybenzene, tolylacetate, 4-chlorophenyl acetate, 2-chloroxylene, bromobenzene, nitrobenzene, nitrotoluene, trichlorobenzene, 4-chlorophenol, 4-methylphenol, phenyl benzoate and others.

The reaction of this invention can be carried out using neat reactants or solutions or dispersions of the reactants. Many of the reactants such as benzene, toluene, xylene, ethylbenzene, phenol and others will be liquid under the reaction conditions employed whereas some highly substituted compounds and condensed ring compounds may be solid and can beneficially be reacted in a solution. Any solvents which do not interfere with the reaction or react with the product or reactants can be used. Examples of suitable solvents include alcohols such as methanol, ethanol and propanol, carboxylic acids such as acetic and benzoic acids, water and aromatic and aliphatic hydrocarbons such as benzene, cyclohexane and iso-octane. Preferred solvents are alcohols and carboxylic acids.

The catalyst system which is used herein is that feature of the invention responsible for converting aromatic compounds to polyaromatic compounds under the relatively mild reaction conditions employed. In its broadest aspects, the catalyst system comprises a mercuric oxyanion compound together with a Group VIII metal or Group VIII metal oxyanion compound.

For the purposes of this invention Group VIII metal oxyanion compound is defined as that compound having an OXY— or —O— radical between the Group VIII metal and the anion.

The mercuric compound can be any compound which is soluble in a solvent capable of being used in the process of this invention and one which preferably does not include halogen ions. Mercuric salts of oxyanions that is those having an oxy- or —O— radical between the mercuric cation and the anion are suitable according to the invention. Oxyanion groups may be selected from groups such as acetate, propionate, sulfate, sulfite, nitrate, phosphate, borate, carbonate and the like. Preferred are those mercuric salts containing organic carboxylates such as, acelate, propionate, octanoate, benzoate, and the like. If salts containing halogen anions are used such as mercuric chloride, same coupled products may result, but the amount of these products will always be less than the amount of mercury present initially. For the catalytic reaction according to the invention to proceed the anion is preferably not selected from a halogen.

The mercuric compound is used in combination with a metal or metal compound of Group VIII in the Periodic System of the Elements. The metals of Group VIII are iron, cobalt, nickel, ruthenium, rhodium, palladium, osmium, iridium, and platinum. Preferred metals of this group are nickel, palladium platinum. Particularly preferred is palladium. The metal can be supplied initially as the free metal. Alternatively, the metal can be supplied as a salt or chelate. Throughout the remainder of this specification, the term "Group VIII metal oxyanion compound" will be used to refer to both the free metal as well as to the salts and chelates of the metal. The metal salts can contain any anion such as those already mentioned as suitable for the mercuric compounds. As with the mercuric compounds, Group VIII metal compounds containing an oxyanion are preferred. Examples of suitable compounds include nickel nitrate, palladium sulfate, platinum acetate, nickel nitrate, palladium sulfate, platinum acetate, nickel formate, palladium propionate, platinum acetylacetonate and complexes of the metal ions with chelating agents such as citric acid, ethylenediaminetetraacetic acid and others. In addition to metal carboxylates such as palladium and platinum acetates and benzoates, the metal halogen-substituted carboxylates constitute another preferred class of Group VIII metal compounds. Examples include bis (trifluoroacetate)palladium, bis (chloroformate) platinum, and bis (chloroacetate) iridium.

In addition to the foregoing two-component catalyst system, a third component can optionally be included. The third component is a compound which functions as a redox agent under the reaction conditions employed. A redox agent is a compound which is capable of being oxidized by one substance in a reaction medium and reduced by another or vice versa, thereby being restored to its original oxidation state. Particularly preferred redox agents are those which can be readily reoxidized to their original state by molecular oxygen. In general, any multivalent metal salt having an oxidation potential more positive than the Group VIII metal, can be used as a redox agent in the process of this invention. In addition, the multivalent metal ion should preferably be present in the salt in a valence state higher than its lowest ionic valence state. The anions of such salts can be the same as, or similar to, the anions present in the mercuric compounds and platinum group metal compounds, i.e., nitrates, sulfates, carbonates, acetates and the like. The multivalent metal with the requisite oxidation potential can be copper, iron, manganese, cobalt, nickel, cerium, uranium, chromium, molybdenum, vanadium and the like. Of the multivalent metal salts, the cupric and ferric salts are preferred. Examples of suitable redox compounds are cupric acetate, ferric acetate, manganese nitrate, cobalt sulfate, nickel formate, cerium acetate, uranium carbonate, chromium nitrate, molybdenum nitrate and vanadium propionate.

The most preferred embodiment of this invention comprises conducting the aromatic coupling reaction in the presence of the three metallic components of the catalyst system, i.e. the mercuric compound, the Group VIII metal or metal oxyanion compound, and the multivalent metal redox compound, and in the presence of a molecular oxygen-containing gas. In this embodiment the reaction is catalytic with respect to all three metallic components. Another way of considering this preferred embodiment is that it comprises the oxidative coupling of aromatic compounds according to the following exemplary reaction:

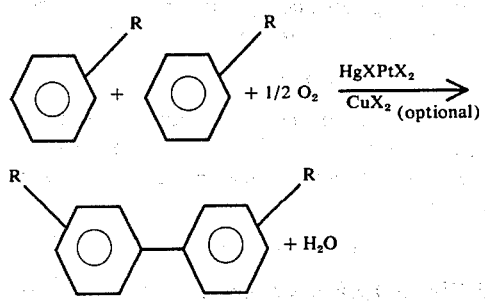

Viewed in this manner, the oxygen is not a component of the catalyst but rather one of the reactants whose reaction with aromatic compounds is catalyzed by the two or three-component catalyst system.

The components of the catalyst system can be present in widely varying amounts. The Group VIII metal component can be present in a concentration from 0.001 molar or less up to 5 molar or more, preferably from about 0.005 to about 1 molar. More preferably a range of from 0.005 to 0.05 molar is particularly useful catalytic amount.

The quantity of mercuric oxyanion compound which is used is expressed in terms of the Group VIII metal compound. The molar ratio of mercuric oxyanion compound to Group VIII metal oxyanion compound is from about 1:10 to about 10:1, preferably from about 1:2 to about 2:1, and more preferably in approximately equimolar amounts.

The quantity of redox reagent which is used may likewise be expressed in terms of the Group VIII metal compound. The molar ratio of redox compound to Group VIII metal compound may vary from 0:1 to about 50:1 preferably from about 0:1 to about 2:1.

The reaction may be run at any temperature, the maximum temperature limitation being that imposed by the thermal stability of the reactants. Preferred reaction temperatures are from 0° to 300° C, more preferably from about 40° to about 200° C.

Reaction pressure, that is the minimal oxygen pressure for the coupling process to proceed as a catalytic reaction is about 200 psi or greater. In general the coupling reaction may proceed under a pressure of from less than one to several hundred atmospheres; however, only a pressure of greater than about 200 psi of oxygen will allow the reaction to become catalytic according to the invention. Suitable pressures above this 200 psi will depend upon the size of the reactor and how much space is available for the molecular oxygen. Any gas containing molecular oxygen such as air or oxygen deluted with other non reactive gases can be used according to the invention as long as the total oxygen partial pressure is above about 200 psi.

In the catalytic method of operation, the reactants can be added to a reactor vessel to which a solution or dispersion of the catalyst mixture is also added. The mixture is brought to a desired temperature and pressure to form the coupled products. After the reaction is terminated, the products can be separated by conventional methods such as crystallization and distillation.

An alternate embodiment of this invention comprises performing the above described reaction heterogeneously over a bed of supported catalyst. The metallic components can be placed on any suitable inert support by standard methods known in the art. The concentration of the catalyst on the support is not critical and may vary widely. The preferred amount is determined by the particular reaction conditions employed, i.e. flow rate of reactants, temperature, size of catalyst bed, desired productivity, etc. The reactants can be vaporized and the gaseous mixture passed over the catalyst in a heated chamber. The temperature should be high enough to maintain a suitable quantity of both reactants and products in the vapor phase but not so high as to decompose either the reactants or products. Typically, temperatures range from 50° to 350° C. Pressures may vary up to 100 atmospheres or more. Reactants may be supplied with or without a diluent gas. Oxygen may be supplied continuously or the oxygen can be supplied through one or more injections into the reaction medium.

The products obtainable from this reaction may vary widely in structure. Two types of coupling are possible via this route. Nuclear to nuclear coupling to form diaromatics connected directly through carbon atoms on the respective aromatic rings is one type of coupling reaction. In this case products have the general formula

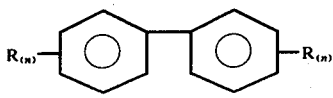

Where R and *n* are as described above in the description of aromatic compounds which may be coupled.

In addition, a second mode of coupling arises when side chain to nuclear coupling occurs. If one of the substituents R' has a removable hydrogen atom, it may be removed during the reaction to couple the aromatic rings through a bridging R' group. Compounds of this type have the general formula

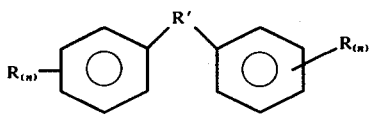

where R and *n* are as before and R' is —$CH_2$—, —$CH_2$—$CH_2$—, —CH=CH—, —$CH_2$—$CH_2$—$CH_2$—,

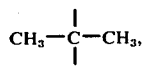

—O—, —S—, —NH—$SO_2$—, and the like.

Also the aromatic group need not be confined to benzene. Condensed ring structure such as naphthalene, anthracene and the like are also coupled by this process as well as heterocyclic aromatics such as pyridine, thiofuran, furan, etc.

It should also be recognized that a single reactant may be coupled to itself to give a symmetrical dimer or a mixture of reactants may be used to cross couple to give unsymmetrical dimers. Also, the coupled products may react further to give trimers, tetramers or even higher polymers.

EXAMPLE 1

In a 200 ml. titanium-lined autoclave 80 ml. of acetic acid, 20 ml. of benzene, 20 grams of phenol, 0.2 grams of mercuric acetate and 0.8 grams of cupric acetate are mixed together. The autoclave is sealed, pressured to 100 psig with pure oxygen and the temperature brought to 80° C. A solution of 0.2 grams of palladium acetate in acetic acid is added to the reactor and the reaction is allowed to continue for four hours. The reaction mixture is then cooled and filtered. Diphenyl, 2-phenylphenol, 4-phenylphenol, dibenzofuran and diphenyl ether are all identified by gas chromatographic analysis.

EXAMPLE 2

The procedure of Example 1 is followed exactly except that 0.4 gram of bis(trifluoroacetate) palladium, PD($OOCF_3$)$_2$, is used instead of the palladium acetate used in Example 1. Gas chromatographic analysis indicates the presence of diphenyl, 2-phenylphenol, 4-phenylphenol, dibenzofuran and diphenyl ether.

EXAMPLE 3

Into a 300 ml. stirred autoclave are placed 100 ml. of toluene, 0.5 grams of palladium acetate and 20 grams of mercuric acetate. The autoclave is sealed, pressured to 300 psi with oxygen and heated to 150° C for several hours. After cooling and venting the gas, the liquid portion is analyzed by gas-liquid chromatography and shown to contain a mixture of 2, 3', 2, 4', 3,3', 3, 4' and 4, 4' dimethyl diphenyl. The selectivity based on consumed benzene is 90% and conversion is 30%.

EXAMPLE 4

A catalyst comprising 2% palladium acetate and 5% mercuric acetate on silica is placed in a heated reactor whose temperature is maintained at 150° C. Toluene and acetic acid are vaporized with a gas stream containing molecular oxygen and the stream passed over the catalyst bed. The liquid condensate collected after reaction is shown by gas-liquid chromatography to contain a mixture of dimethyl biphenyl as well as benzyl acetate.

EXAMPLE 5

A reaction conducted as in Example 3 is carried out except that the toluene is replaced by anisole. Gas-liquid chromatographic analysis of the resultant solution indicates the presence of at least three isomers of dimethoxydiphenyl.

EXAMPLE 6

A reaction conducted as in Example 3 is carried out except that the toluene is replaced by methyl benzoate. Biphenyl dicarboxylic acid and biphenyl dimethyl ester is the major product.

EXAMPLE 7

A reaction conducted as in Example 3 is carried out except that the toluene is replaced by ethylbenzene. Diethyl biphenyl was formed along with acetophenone, phenylacetaldehyde and a small amount of phenethyl acetate.

EXAMPLE 8

An experiment performed as in Example 3 is carried out except that the toluene is replaced with xylene. A mixture containing tetramethyl biphenyls and methylphenyldimethylphenyl methanes is obtained.

EXAMPLE 9

An experiment performed as in Example 1 is carried out except that the toluene is replaced with naphthalene. A mixture of binaphthalene and ternaphthalene is obtained.

EXAMPLE 10

An experiment performed as in Example 1 is carried out except that toluene is replaced by phenyl ether. One of the products is determined to be diphenoxy biphenyl.

EXAMPLE 11

Biphenyl is coupled as in Example 1 to form tetraphenyl in high yield.

EXAMPLE 12

Chlorobenzene is coupled to form a mixture of diclorobiphenyl isomers according to the procedure set forth in Example 1.

EXAMPLE 13

Nitrobenzene is coupled according to the procedure set forth in Example 1 to form dinitrobiphenyl.

EXAMPLE 14

A catalyst comprising 0.04 moles palladium acetate and 0.04 moles mercuric acetate an silica is placed into a reactor vessel continning 10.4 mols. toluene and having variable pressure control. The catalyst system is used to couple the toluene at 150° C with the results tabulated in table 1 wherein the oxygen pressure was varied from 50 psi to 550 psi. Table 1 includes the results of eleven runs wherein the only parameter varied was oxygen pressure.

TABLE 1

| | Effect of Oxygen Pressure | | | |
|---|---|---|---|---|
| Run Number | Oxygen Pressure | Rate Moles/Liter/Hour Product | Conversion | Selectivity | Total Moles Bitolyls |
| 1 | 50 | — | 8.5 | — | 0.001 |
| 2 | 100 | — | 2.4 | — | 0.001 |
| 3 | 150 | — | 1.8 | — | 0.001 |
| 4 | 200 | — | 1.6 | — | 0.001 |
| 5 | 250 | 0.001 | 4.2 | 2.6 | 0.006 |
| 6 | 300 | 0.158 | 20.4 | 56.8 | 0.631 |
| 7 | 350 | 0.202 | 24.4 | 60.4 | 0.807 |
| 8 | 400 | 0.236 | 28.6 | 60.8 | 0.945 |
| 9 | 450 | 0.281 | 33.3 | 62.3 | 1.126 |
| 10 | 500 | 0.315 | 37.7 | 61.6 | 1.262 |
| 11 | 550 | 0.345 | 41.0 | 62.0 | 1.382 |

The data of Table 1 clearly demonstrate that although less than stoichiometric amounts of bitolyls result at lower oxygen pressure, however at oxygen pressure greater than about 200 psi, more than stoichiometric amounts of bitolyls are produced based on the catalyst present.

EXAMPLE 15

A reactor vessel is charged with 0.04 moles of palladium acetate, 0.20 moles of mercuric acetate and 10 moles of benzene under an oxygen pressure of 550 psi, at a temperature of 150° C. The coupling reaction conditions are maintained for 4 hours with the following halogen presences demonstrated by runs 2 through 6 of table 2.

TABLE 2

| | Effective of Halogen Pressure | | | |
|---|---|---|---|---|
| Run Number | Additive | Amount Moles | Rate* Moles Product/ Liter/Hour | Total Moles Bitolyls |
| 1 | None | — | 0.291 | 3.6 |
| 2 | HCl | 0.167 | 0.003 | 4.1 |
| 3 | HCl | 1.67 | 0.002 | 3.7 |
| 4 | NaCl | 0.2 | 0.006 | 2.1 |
| 5 | HgBR₂ | 0.2 | 0.006 | 3.1 |
| 6 | Pd Cl₄ | 0.2 | 0.002 | 2.8 |

*A rate of less than 0.01 indicates that the reaction is not of a catalytic type.

The data of table 2 illustrates that a stoichiometric reaction is possible in the presence of a halogen ion; however a catalytic reaction based on the amount of catalyst present is achieved only in the absence of the halogen additives.

EXAMPLE 16

A reactor vessel is charged with 10 moles of benzene, 0.04 moles palladium acetate, and various amounts of sulfuric acid or mercuric acetate as illustrated in table 3 below. Coupling reaction conditions are maintained constant with the temperature at 150° C and the oxygen pressure at 300 psi.

TABLE 3

| Run Number | Palladium Acetate Moles | Sulfuric Acid Moles | Mercuric Acetate Moles | Rate Moles Product/ Liter/Hour |
|---|---|---|---|---|
| 1 | 0.04 | — | — | 0.04 |
| 2 | 0.04 | 1.0 | — | 0.19 |
| 3 | 0.04 | — | 0.04 | 0.28 |

The results of table 3 demonstrate the superior effect of mercuric acetate as compared to sulfuric acid under identical conditions.

EXAMPLE 17

A reactor vessel is charged with 10 moles of toluene, 0.04 moles palladium acetate under constant temperature (150° C) and oxygen pressure of 300 psi. As illustrated in table 4 below, run 1 utilized 1.0 mole of sulfuric acid and run 2 utilized 0.04 moles of mercuric acetate for comparative purposes.

TABLE 4

| Run Number | Palladium Acetate Moles | Sulfuric Acid Moles | Mercuric Acetate Moles | Bitolyls (Product) | Other Products benzoic acid, benzyl acetate benzaldehyde |
|---|---|---|---|---|---|
| 1 | 0.04 | 1.0 | — | 0.670 | 1.0 |
| 2 | 0.04 | — | 0.04 | 0.801 | 0.008 |

The results of Table 4 demonstrate the superior use of mercuric acetate according to the invention as compared to the sulfuric acid which is not according to the invention process, Table 4 also indicated the weakness of the acid system, that is, the increased side reactions of substituted benzenes.

Obviously, many modifications and variations of the invention, as hereinabove set forth, can be made without departing from the spirit and scope thereof, and only such limitations should be imposed as are indicated in the appended claims.

What is claimed is:

1. A catalytic process for coupling aromatic compounds of the formula

where
n is an integer from 0 to 5 and each of the R groups is hydroxy, alkoxy, alkyl, aryloxy, aryl, acyl, alkanoate, carboxyl, carboxylic esters, halogen or nitro, and where two R groups, located on adjacent carbon atoms of the benzene ring, can be joined to form a carbocyclic or heterocyclic ring with molecular oxygen to produce coupled aromatic compounds comprising coupling said aromatic compounds with at least about 200 psi molecular oxygen in the presence of a mercuric oxyanion compound and a Group VIII metal or Group VIII metal oxyanion compound.

2. A process according to claim 1 wherein said integer $n$ is 0 to 1.

3. A process according to claim 2 wherein said integer $n$ is one and said R group is hydroxy, alkoxy or aryloxy.

4. A process according to claim 1 wherein at least one R group is alkyl.

5. A process according to claim 4 wherein said alkyl group is methyl.

6. A process according to claim 1 wherein at least a portion of said aromatic compounds is phenol.

7. A process according to claim 1 wherein at least a portion of said aromatic compounds is benzene.

8. A process according to claim 1 wherein at least a portion of said aromatic compounds is toluene.

9. A process according to claim 1 wherein at least one of said R groups is carboxyl or carboxylic ester.

10. A process according to claim 1 wherein at least a portion of said aromatic compounds is diphenyl ether.

11. A process according to claim 1 wherein said Group VIII metal or Group VIII metal oxyanion compound is a metal oxyanion compound.

12. A process according to claim 11 wherein the metal component of said Group VIII metal oxyanion compound is palladium.

13. A process according to claim 11 wherein the Group VIII metal oxyanion compound is a palladium oxy-salt.

14. A process according to claim 11 wherein said Group VIII metal oxyanion compound is a palladium carboxylate.

15. A process according to claim 1 wherein said mercuric oxyanion compound is a mercuric oxy-salt.

16. A process according to claim 1 wherein said mercuric oxyanion compound is a mercuric carboxylate.

17. A process according to claim 1 wherein the reacting of said aromatic compound with molecular oxygen is conducted in the presence of a mercuric oxyanion compound, a Group VIII metal or metal oxyanion compound, and redox compound capable of oxidizing the Group VIII metal and capable of being oxidized by molecular oxygen.

18. A process according to claim 17 wherein said redox compound is a ferric or cupric salt.

19. A process according to claim 18 wherein said redox compound is a ferric or cupric carboxylate.

20. A process for coupling aromatic compounds of the formula

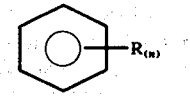

where $n$ is an integer from 0 to 1 and the R group is hydroxy, alkoxy, carboxyl, alkyl, aryl, aryloxy or halogen, comprising reacting said compounds with at least about 200 psi molecular oxygen in the presence of a catalyst system comprising a mercuric oxy-salt, a Group VIII metal oxy-salt and a redox agent.

21. A process according to claim 20 wherein said Group VIII metal oxy-salt is a palladium oxy-salt and said redox agent is a cupric or ferric salt.

22. A process according to claim 20 wherein said catalyst system comprises mercuric acetate, palladium acetate and cupric acetate.

23. A process according to claim 1 wherein the reaction is conducted homogeneously in the liquid phase.

24. A process according to claim 1 wherein the reaction is conducted heterogenously in the gas phase.

25. A process according to claim 1 wherein said aromatic compound is toluene and at least one of the products is dimethyl biphenyl.

26. A process according to claim 1 wherein said aromatic compound is benzoic acid or an ester thereof and at least one of the products is dicarboxylic acid diphenyl or an ester thereof.

27. A process according to claim 1 wherein said aromatic compound is xylene and the products are tetramethyl biphenyl and methylphenyl-dimethylphenyl methane.

28. A process according to claim 1 wherein said aromatic compound is anisole and at least one of the products is dimethyl biphenyl.

29. A process according to claim 1 wherein said aromatic compound is ethylbenzene and at least one of the products is diethyl biphenyl.

30. A catalytic process for coupling aromatic compounds of the formula

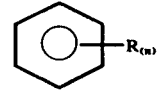

where
$n$ is an integer from 0 to 5 and each of the R groups is hydroxy, alkoxy, alkyl, aryloxy, aryl, acyl, alkanoate, carboxyl, carboxylic esters, halogen or nitro, and where two R groups, located on adjacent carbon atoms of the benzene ring, can be joined to form a carbocyclic ring with molecular oxygen to produce coupled aromatic compounds comprising coupling said aromatic compounds with at least about 200 psi molecular oxygen in the presence of a mercuric oxyanion compound and a Group VIII metal or Group VIII metal oxyanion compound.

* * * * *